United States Patent [19]

Businger

[11] Patent Number: 5,067,356
[45] Date of Patent: Nov. 26, 1991

[54] CONDITIONAL SAMPLING TECHNIQUE FOR FLUX MEASUREMENT

[75] Inventor: Joost A. Businger, Anacortes, Wash.

[73] Assignee: University Corporation for Atmospheric Research, Boulder, Colo.

[21] Appl. No.: 485,152

[22] Filed: Feb. 26, 1990

[51] Int. Cl.$^5$ .............................................. G01N 1/00
[52] U.S. Cl. ................................................ 73/863.02
[58] Field of Search .................. 73/170 R, 188, 189, 73/863.01, 863.02, 863.03, 863.31, 863.83, 864.34, 864.81, 432.1

[56] References Cited

U.S. PATENT DOCUMENTS

| | | | |
|---|---|---|---|
| 3,299,700 | 1/1967 | Stout, Jr. | 73/170 R |
| 3,866,474 | 2/1975 | Hasselmann | 73/864.34 |
| 4,890,488 | 1/1990 | Pincent et al. | 73/189 |

FOREIGN PATENT DOCUMENTS 1288531  2/1987  U.S.S.R. ............................ 73/863.01

OTHER PUBLICATIONS

Desjardins, R. L., Description and Evaluation of a Sensible Heat Flux Detector, *Boundary Layer Meteorology* 11, pp. 147-154 (1977).
Hicks, B. B. and McMillan, R. T., A Simulation of the Eddy-Accumulation Method for Measuring Pollutant Fluxes, 23, *Journal of Climate and Applied Meteorology*, pp. 637-643 (Apr. 1984).

*Primary Examiner*—Robert Raevis
*Attorney, Agent, or Firm*—Dorr, Carson, Sloan & Peterson

[57] ABSTRACT

A conditional sampling technique for flux measurement involves measuring vertical velocity of the movement of air or gas, collecting samples of the air and its components in an "up" canister when the vertical velocity in the upward direction exceeds a threshold, and collecting samples in a "down" canister when the vertical velocity in the downward direction exceeds a threshold. Sensing intervals for measuring and collecting are repeated for a predetermined sampling time period. The passageways to the canisters are always either fully closed or fully opened. At the end of the sampling time period, the standard deviation of the vertical velocities is calculated, and the concentration of a particular component in the samples collected in the canisters is determined by chemical or other analysis. The flux of that component is determined by multiplying a newly discovered coefficient of proportionality and the standard deviation and the difference in concentrations of the particular component collected in the up and down canisters.

18 Claims, 4 Drawing Sheets

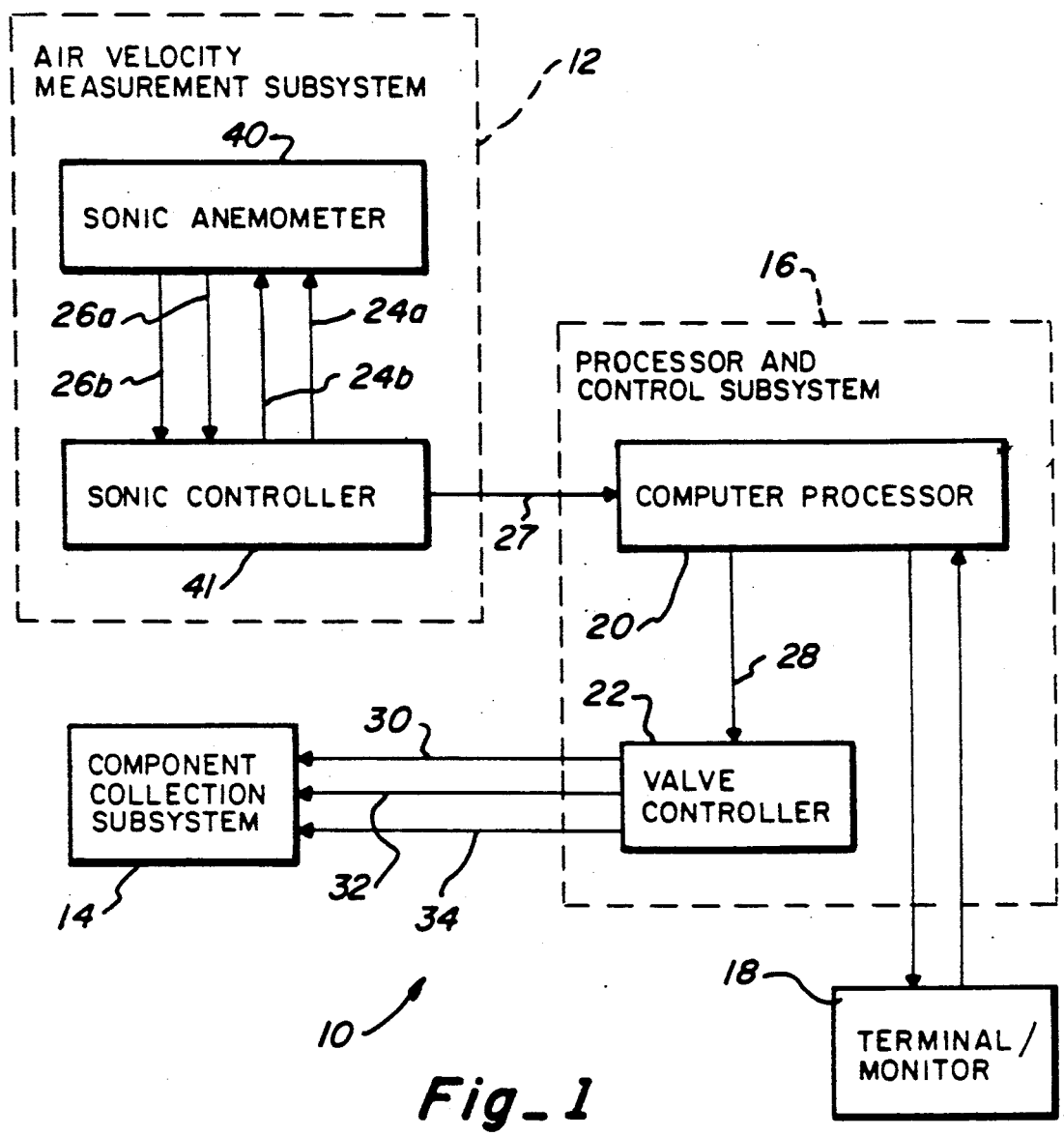
Fig_1
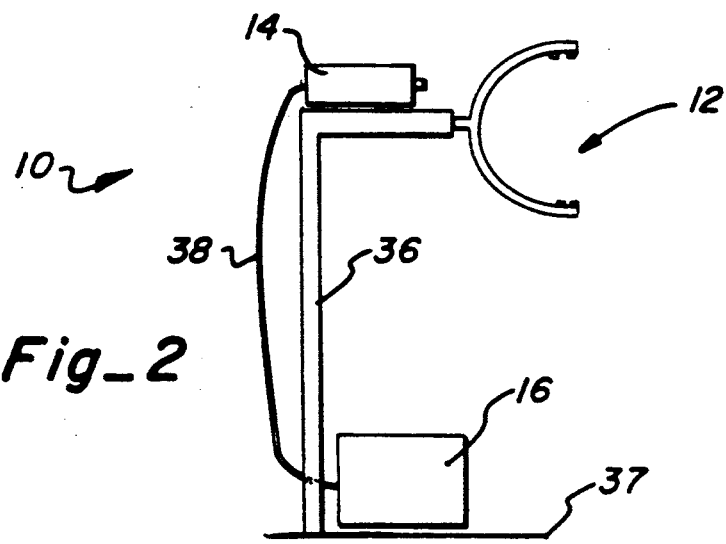
Fig_2

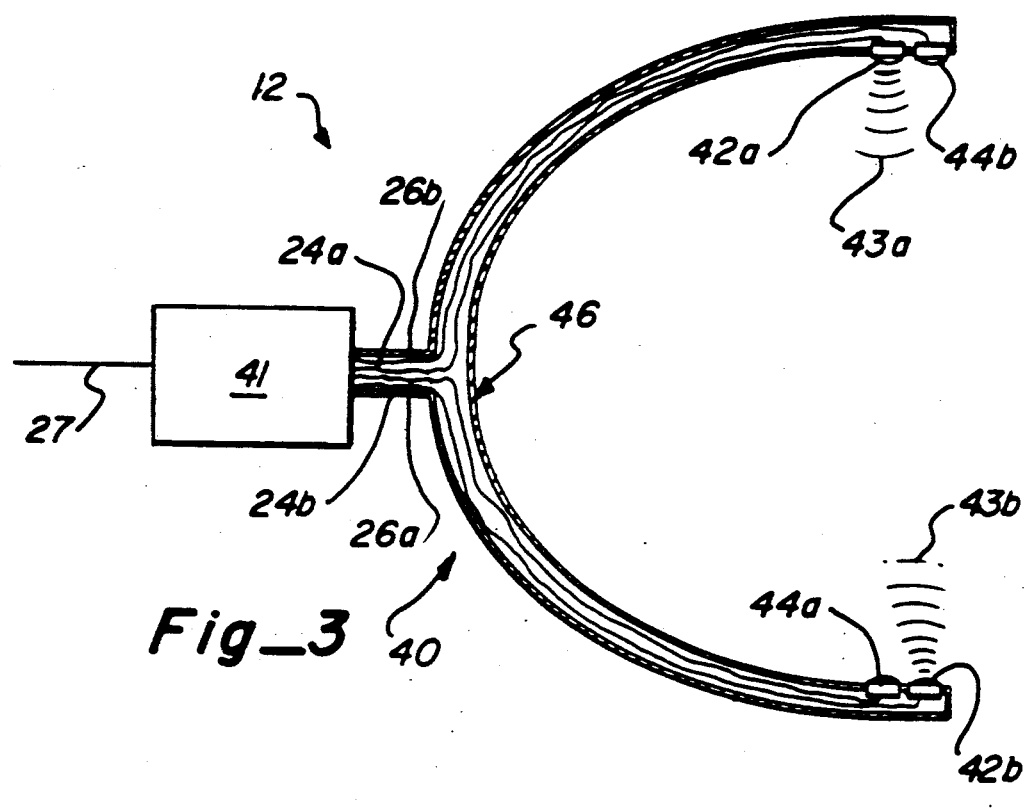
Fig_3
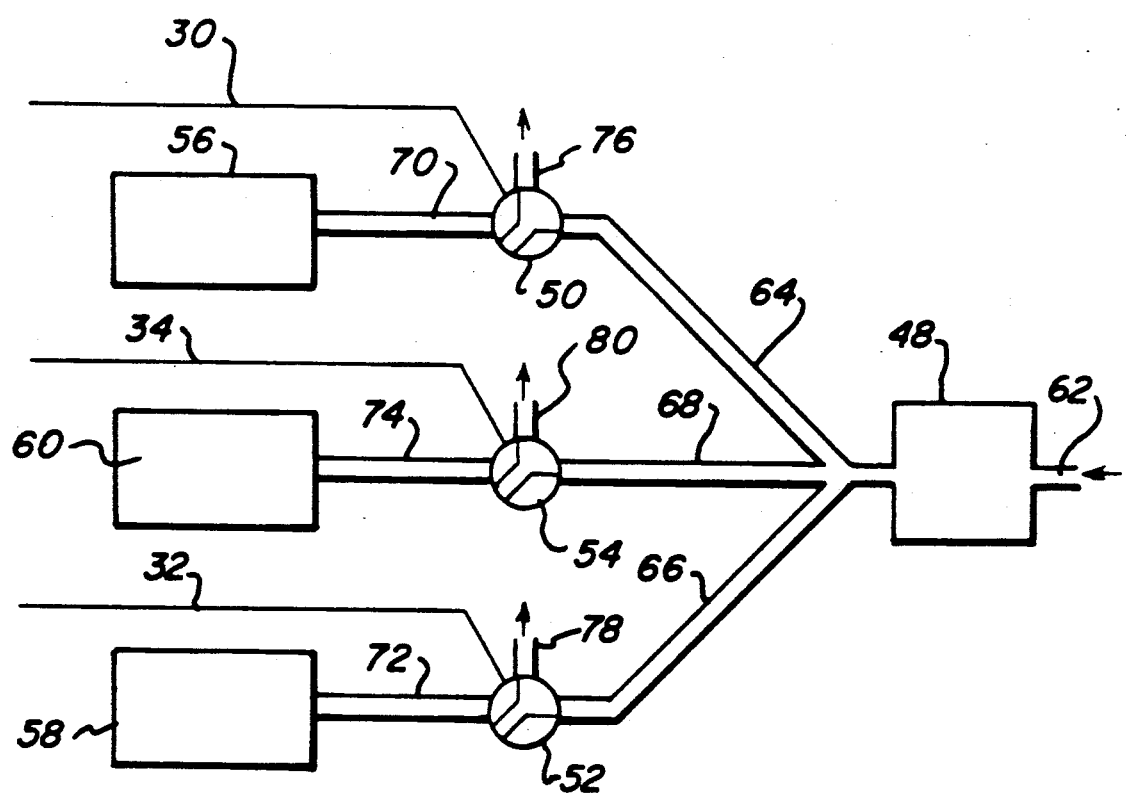
Fig_4

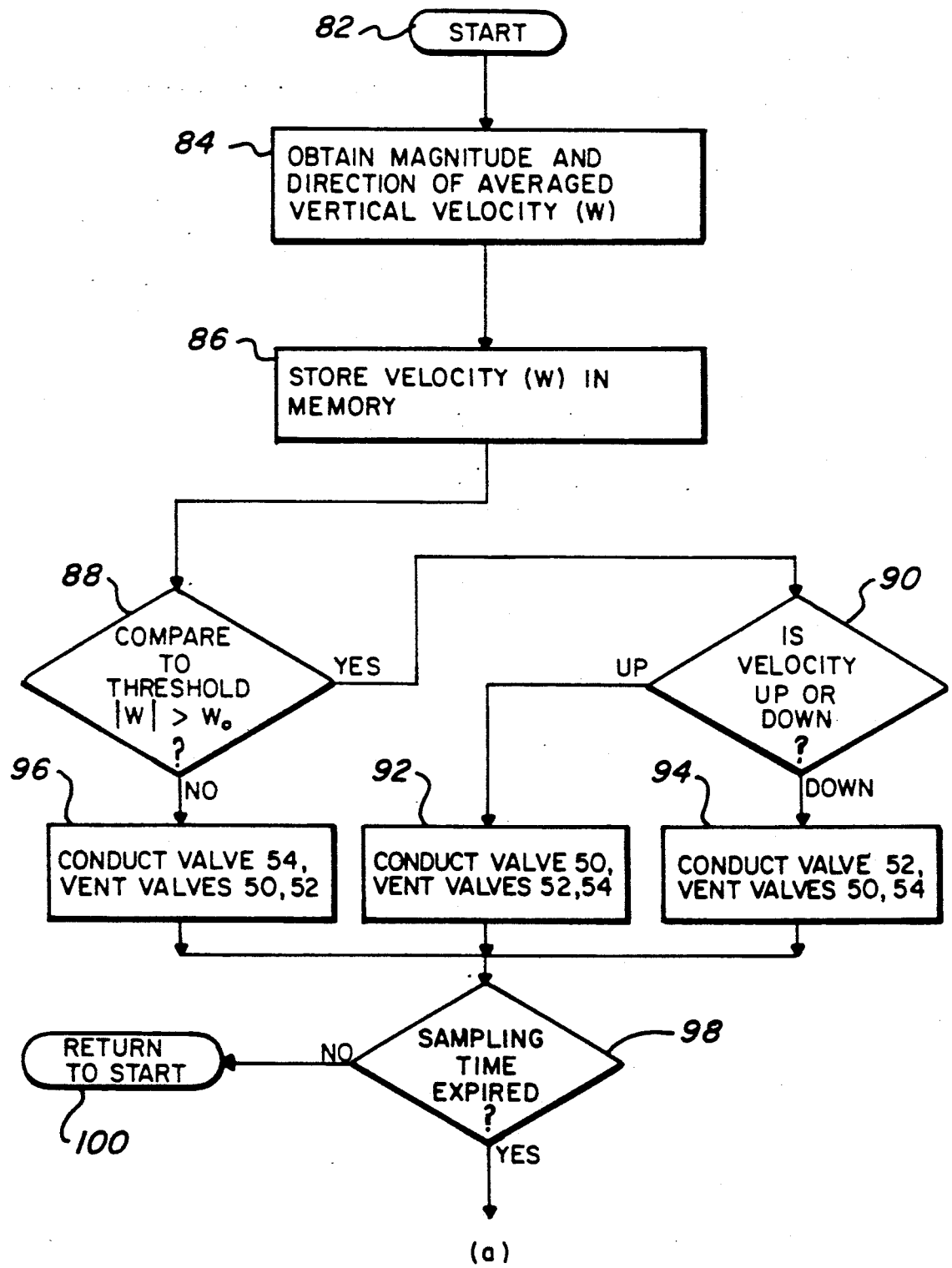
Fig_5A

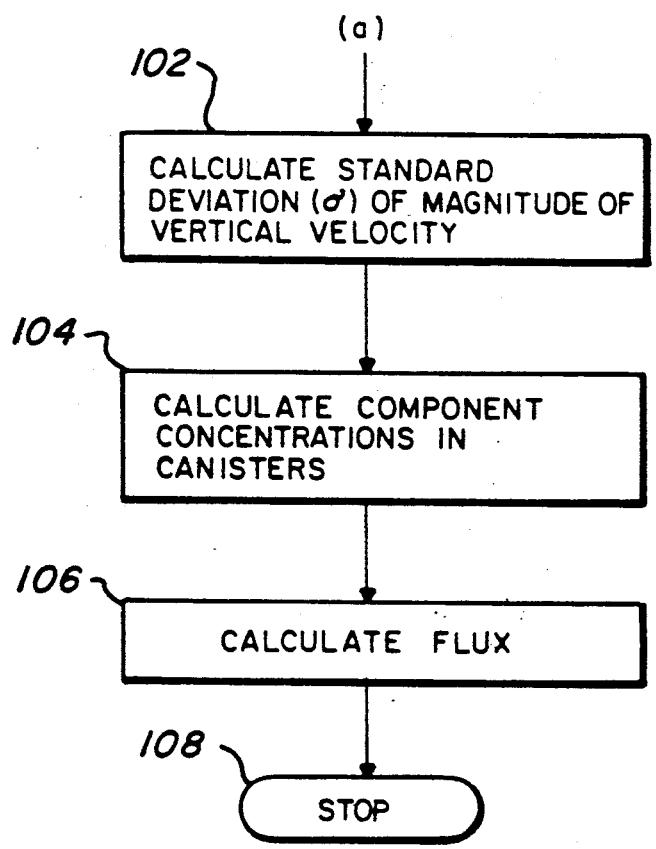
Fig_5B
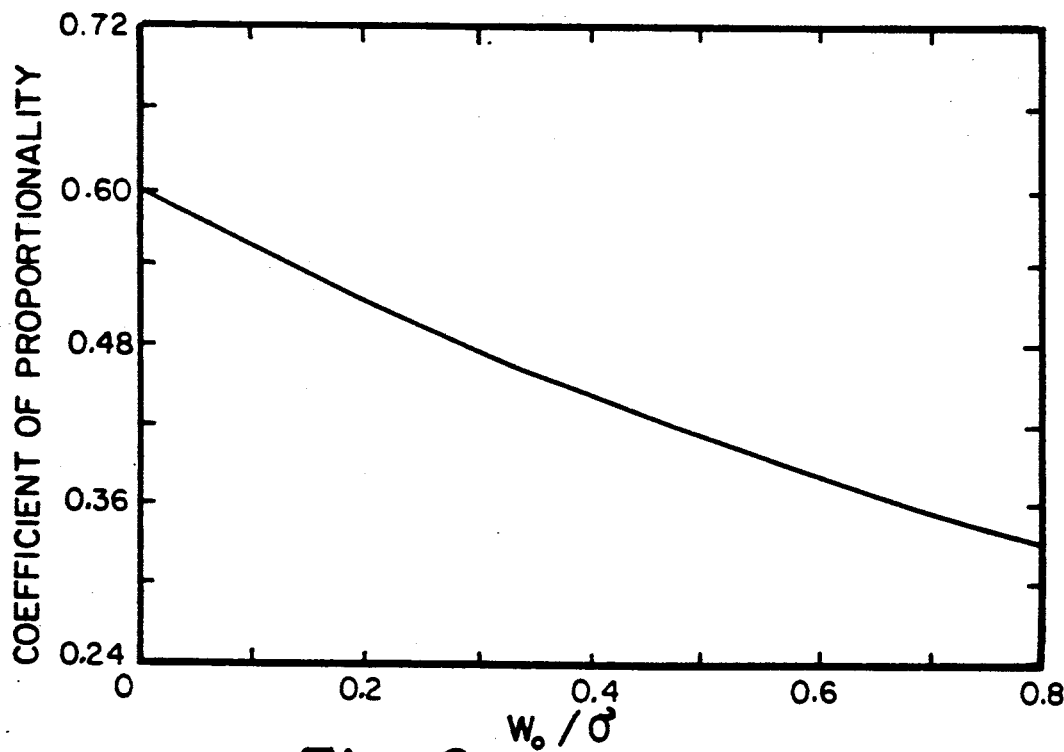
Fig_6

CONDITIONAL SAMPLING TECHNIQUE FOR FLUX MEASUREMENT this invention was made with U.S. government support under the Cooperative Agreement dated Oct. 2, 1987 and any amendments thereto, between the assignee of this invention, the University Corporation for Atmospheric Research and the National Science Foundation. The U.S. government has certain rights in this invention.

This invention relates to the sampling and measurement of flux. More particularly, the present invention relates to a new and improved method and apparatus for obtaining samples and measuring flux according to a newly discovered technique.

BACKGROUND O THE INVENTION

Recently recognized environmental concerns have suggested a need to measure the chemical constituents, carried components, qualities and characteristics of the air (hereinafter components) moving down from the atmosphere toward the earth's surface and up from the earth's surface toward the atmosphere. Vertical "flux" is a term used to describe the quantity of a selected component carried by the air or a gas passing through a given horizontal level or area in a given time. Among other things, flux information is used to calculate and predict environmental impacts on the earth's surface and to the atmosphere, such as acid rain, ozone, methane and carbon monoxide, as examples. Meteorologists employ flux measurements in deriving and predicting certain weather and meteorological information, such as influences from temperature, humidity and airborne particulate matter, as examples. A variety of other known applications for flux measurement now exist.

Simply stated, flux measurement involves sensing the vertical velocity of the gas or air movement, measuring the concentration of a desired component carried by the air in each direction of sensed air movement, multiplying the vertical air velocity by the component concentration measured to obtain the amount or quantity of the component transferred in each direction, and algebraically summing the measured amounts transferred upward and downward over a period of time to obtain the net amount of the component transferred in one direction or the other, i.e. the flux of that component. Although simple enough to understand in concept, a number of practical difficulties have made accurate flux measurement for all types of components impossible or extremely difficult to achieve.

One known flux measurement technique is the instantaneous or eddy correlation technique. The instantaneous technique follows the procedure outlined above, but its application is limited to those components for which there are sensors capable of instantaneously, or very rapidly, measuring the concentration of the desired component. This is a serious limitation because the sensors which are capable of instantaneous measurement are responsive to only a few of the components for which flux measurements are desired. For example, flux measurements of temperature and humidity can be instantaneously achieved, because temperature and humidity sensors capable of measuring or responding on a nearly instantaneous basis are currently available. Instantaneous measurements are required because the measured concentration of the component must be correlated to the vertical velocity of the air movement, which may fluctuate rapidly and repeatedly over the course of time while the flux measurement occurs. Presently, it is believed that no more than about five to ten different types of sensors exist which are capable of responding instantaneously for flux measurement purposes. Accordingly, the instantaneous technique is severely limited in its applicability, because scientists desire to measure the flux of many more components than just those few components for which instantaneously-responsive sensors are available.

To avoid the problem or limitation created by the unavailability of instantaneous sensors, a component sampling technique known as eddy-accumulation has been developed for use in flux measurement. The eddy-accumulation sampling technique uses two reservoirs or canisters to collect samples of air containing the component, and the air samples are later analyzed by laboratory techniques which do not require instantaneous sampling. One canister is used to accumulate samples from the upward moving air, and the other canister accumulates samples from the downward moving air. In order for the eddy-accumulation sampling technique to be accurate, the rate of sample accumulation in each canister must be proportional to the magnitude of the vertical velocity. Proportional accumulation in each canister is achieved by a valve which attempts to quickly and accurately vary the size of the passageway into the canister in proportion to the magnitude of the vertical velocity of the air.

The drawback of eddy-accumulation sampling lies in the practical difficulty of accurately controlling the size of the passageway to the canisters. This problem has proved to be so difficult to overcome that flux measurements from eddy-accumulation sampling have not been accepted as fully reliable or accurate. Thus, while the eddy-accumulation sampling is theoretically available to determine fluxes of a wide variety of components, its accuracy is problematical. Consequently flux measurements based on eddy-accumulation sampling have met with only very limited acceptance.

It is with regard to the desire to achieve accurate component sampling and a flux measurement technique that obtains the advantages and avoids the disadvantages of the instantaneous and eddy-accumulation sampling techniques, that the present invention has resulted.

SUMMARY OF THE INVENTION

The present invention relates to a new conditional sampling technique and the measurement of flux using that technique. Air or gas samples containing the desired component are collected in a reservoir means without requiring proportional control over the size of the passageway to the canister. Accurate measurement of the flux of the particular component is nevertheless obtained by the use of a newly discovered mathematical relationship which involves a coefficient and the multiplication of the standard deviation of the vertical air velocity by the component concentration difference in the two reservoirs.

In accordance with one significant aspect of the present invention, an apparatus and a method for conditionally sampling a particular component carried by the air involves measuring the vertical velocity and collecting separate samples of the air with its carried components when the air movement is in the up and down directions. The samples are collected under conditions where the passageways to the reservoir means are fully unrestricted when the sample is admitted, thereby avoiding the difficulties and uncertainties of proportional valving. Collecting the samples in this manner is acceptable because the flux is calculated utilizing a newly discovered mathematical relationship which takes into consideration the manner in which the samples were collected.

In accordance with another significant aspect of the present invention, the flux of the particular component is measured or calculated by determining the standard deviation of the values of the vertical velocity of the air movement measured. The vertical velocity is measured during each of a number of regularly occurring sensing intervals during which samples are collected over a predetermined sampling time period. The concentrations of the particular component are determined from chemically analyzing the up and down air movement samples collected in the reservoir means. The flux measurement is calculated by multiplying the standard deviation of the vertical velocity by the difference in the up and down concentrations, and this product is further multiplied by a coefficient of proportionality, which in many cases is approximately 0.6. It has been discovered that the use of this coefficient obtains, for most atmospheric conditions, an accurate value of the flux under the sample collecting conditions wherein the inlet to the sample collecting means are not proportionally controlled, as in the prior art eddy-accumulation technique. The advantage of being able to analyze the component in the sample collection means at a later time in a laboratory is retained in the present technique, thereby allowing the present invention to be used to obtain more accurate measurements of the flux of a wide variety of different components.

A more complete understanding and appreciation of the present invention can be obtained by reference to the accompanying drawings, which are briefly described below, from the following detailed description of presently preferred embodiment, and from the appended claims.

BRIEF DESCRIPTION OF THE DRAWINGS

FIG. 1 is a block diagram of the components of the apparatus used for conditional sampling of a component, the flux of which is desired to be measured, according to the present invention.

FIG. 2 is a simplified illustration of the apparatus shown in FIG. 1 in a condition of actual use.

FIG. 3 is an illustration of the air velocity measurement subsystem, shown in FIGS. 1 and 2.

FIG. 4 is a generalized illustration of the component collection subsystem, shown in FIGS. 1 and 2.

FIGS. 5a and 5b are portions of a flow diagram of the operations performed by the processor and control subsystem shown in FIGS. 1 and 2, to obtain samples of the component in the component collection subsystem, and to calculate the flux measurement according to the present invention.

FIG. 6 is a graph of the coefficient of proportionality of the present invention plotted versus the ratio of a vertical velocity threshold to the standard deviation of the vertical velocity, for use in the calculation of the flux measurement according to the operations shown in FIGS. 5a and 5b.

DETAILED DESCRIPTION

A presently preferred embodiment of an apparatus 10 for conditional sampling of a component, carried by the movement of air or gas, to be used in calculating the flux measurement of that component is shown in FIG. 1. The apparatus 10 comprises an air velocity measurement subsystem 12, a component collection subsystem 14, a processor and control subsystem 16, and an optional terminal/monitor 18.

The air velocity measurement subsystem 12 includes means for sensing the magnitude and direction of the vertical component of the air velocity, known as vertical velocity. The magnitude and direction of the vertical velocity are measured at a predetermined periodic sampling rate of 200 samples per second, for example, which is one sample every 5 milliseconds. Once every 100 milliseconds the previous 20 samples, for example, are averaged to create an averaged value of vertical velocity referred to herein as W. This 100 millisecond sensing interval is repeated for a predetermined sampling time period during which the samples are collected. In this example, the sensing interval occurs every tenth of a second and the predetermined sampling time period may extend for 30 minutes.

The component collection subsystem 14 collects samples of air in reservoir means such as containers, bags or other suitable sample collection canisters. After the predetermined sampling time period, the canisters are removed and the concentration of the component accumulated in the canisters is determined from analysis, usually in a chemical laboratory. One canister is used for collecting samples from air with an upward vertical velocity, referred to as "up" samples. A second canister is used for collecting samples from air with a downward vertical velocity, referred to as "down" samples. A third canister is used for collecting samples from the air when the averaged value of vertical air velocity is near zero, or below a predetermined threshold, to determine the ambient concentration of the component. Passageways or inlets to the three canisters are opened fully without restriction to allow a sample to enter the canister, and the passageways close after the sample has been collected. The collected samples are thus trapped in the canisters until the canisters are opened for analysis of the components contained therein.

The processor and control subsystem 16 includes a computer processor 20 which performs the various calculating, information storage and retrieval, control and processing functions described below. The processor 20 receives from the air velocity measurement subsystem 12, a gas movement signal 27 representative of the averaged value of the magnitude and direction of the vertical air velocity once during each repetitive sensing interval. The values representative of this magnitude and direction are stored in a memory (not shown) of the processor 20 for later use in determining the flux measurement. The values representative of the magnitude of the vertical velocity are also compared to a predetermined threshold limit. If the vertical velocity exceeds the threshold limit, command signals 28 are delivered to the valve controller 22. In response to the command signals 28, the valve controller 22 delivers valve control signals 30, 32 and 34 to the component collection subsystem 14. The valve control signals open and close valves in the passageways to the canisters, as described in greater detail below. Alternatively, in some circumstances the processor 20 could deliver the valve control signals 30, 32 and 34 directly to the valves, in which case the valve controller 44 would be unnecessary. The functions performed by the air velocity measurement subsystem 12, the processor 20 and the valve controller 22 could be divided differently than that shown and described herein, or possibly even be achieved by components integrated more than shown and described, while still maintaining the same essential functionality of the present invention.

The terminal/monitor 18 is connected to the processor 20 to allow interaction by a human operator. The operations of the processor 20 and consequently, the apparatus 10, can be controlled and monitored from the terminal/monitor 18. Various parameters of the operation can be set and controlled at the terminal/monitor 18. For example the frequency of the sensing intervals, the threshold limits of vertical velocity, and the sampling time period can all be set or adjusted at the terminal/monitor 18.

The apparatus 10 is shown in FIG. 2 in a condition of typical use. The air velocity measurement subsystem 12 and component collection subsystem 14 are mounted at the top of a mast 36 above the surface 37 of the earth. The mast 36 and subsystems 12 and 14 are located where it is desirable to measure the flux of some component. For example, the apparatus 10 may be measuring the flux of carbon dioxide several meters above an agricultural field of interest. The processor and control subsystem 16 is preferably located on or near the ground. A cable 38 contains conductors which carry the signals 27, 30, 32 and 34 (FIG. 1) between the processor and control subsystem 16 and the component collection subsystem 14 and the air velocity measurement subsystem 12 at the top of the mast 36. Other types of use arrangements and orientations could be employed. For example, the collection subsystem 14 could be located on the ground with a long inlet tube running down from the top of the mast to the components on the ground.

More details of the air velocity measurement subsystem 12 are apparent from FIG. 3. The means for measuring the magnitude an direction of the vertical air velocity preferably takes the form of a commercially available sonic anemometer 40, and an associated sonic controller 14. The sonic anemometer 40 utilizes two sonic transmitters 42a and 42b and two sonic receivers 44a and 44b. Sonic transmitters 42a and 42b transmit an ultrasonic frequency which is preferably within the range of about 40 to 300 kHz. Transmitter and receiver pairs 42a,44a and 42b,44b are positioned in a spaced apart facing relationship on a frame 46. The transmitter/receiver pairs are vertically separated by a predetermined fixed distance, and the orientation of the frame 46 positions the transmitters 42a and 42b directly vertically above and below the receivers 44a and 44b, respectively. The transmitter 42a transmits sonic waves in a vertically down direction and the receiver 44a receives its transmitted sonic waves. Similarly, the transmitter 42b transmits sonic waves in a vertically up direction and the receiver 44b receives its transmitted sonic waves.

Operation of the sonic anemometer 40 is controlled by the sonic controller 41 and is understood by reference to FIGS. 1 and 3. The measurement of the magnitude and direction of the vertical air velocity commences with the sonic controller 41 delivering a signal 24a to one of the transmitters, for example transmitter 42a. Transmitter 42a is immediately energized and transmits a sonic wave or wavefront 43a toward the receiver with which it communicates, in this example receiver 44a. Immediately upon receipt of the transmitted sonic wavefront the receiver 44a sends a signal 26a to the sonic controller 41. The sonic controller measures the time difference between delivery of the signal 24a and receipt of the signal 26a, and obtains a time value representative of the time required for the sonic wave to travel downward through the air from the upper transmitter to the lower receiver. This value is the "down" time value. The same sequence of steps is performed simultaneously using the other communicating transmitter and receiver pair, in this example 42b and 44b, and the other signal pair 24b and 26b, to obtain an "up" time value. The up time value represents the time required for the sonic wave or wavefront 43b to travel upward through the air from the lower transmitter 42b to the upper receiver 44b.

The vertical movement of the air increases the time required for one sonic wavefront to traverse the distance between the communicating transmitter and receiver, in the case of a "headwind", and reduces the time required for the other sonic wavefront to traverse the distance between the communicating transmitter and receiver, in the case of a "tailwind." The sonic controller 41 compares the up time value and the down time value and determines from the comparison whether the air movement is upward or downward. The sonic controller also subtracts the up and down values, and this difference represents the vertical velocity, if any.

The sonic controller 41 preferably includes a processor and look-up table in memory from which to obtain the value of the vertical velocity, or otherwise calculates the vertical velocity from the difference in the up and down time values, and the distance between the separated transmitter/receiver pairs on the frame 46. The calculations of vertical velocity are preferably made every 5 milliseconds. Every 100 milliseconds a calculation is made to average the past 20 values to give the averaged value of vertical velocity W, called the gas movement signal. This gas movement signal 27, representative of the magnitude and direction of the averaged value, is supplied to the computer processor 20 where it is used to control the valves of the component collection subsystem 14 and is also stored in memory for later use, as explained below.

An alternate arrangement of the sonic anemometer 40 may use only a pair of separated transceivers facing one another on the frame 46, rather than two separate pairs of communicating transmitters and receivers. As can be appreciated, the two transceivers are able to accomplish the same functions as have previously been described for the two transmitter/receiver pairs.

A sonic anemometer and its associated controller which have proved satisfactory to practice the present invention is Applied Technologies, Inc., Part Number SWS 211/1S. This anemometer has the separated transceivers feature. A variety of other types of devices are available for measuring vertical velocity, including a hot-wire anemometer, a vertically-oriented propeller anemometer, a gust probe and many others.

More details of the component collection subsystem 14 are shown in FIG. 4. The subsystem 14 preferably utilizes a pump 48, three valves 50, 52 and 54, and three canisters 56, 58 and 60. The pump 48 pulls air in through an inlet 62 and pushes the air through tubes 64, 66, 68 to the valves 50, 52 and 54, respectively. The valves 50, 52 and 54 are two-way valves and can direct the air from the tubes 64, 66 and 68 to passageways 70, 72 and 74 leading to the canisters 56, 58 and 60, respectively, in one operative position referred to herein as the conductive position. When a valve is in the conductive position the valve is open substantially fully without restriction to allow air to flow through from the tube to the passageway and into the canister. The valves 50, 52 and 54 can vent the air to the surrounding environment through vent pipes 76, 78 and 80, respectively, in the other operative position referred to herein as the vent position. When a valve is in the vent position the valve is closed to fully terminate the flow of air from the tube to the passageway and into the canister.

The valves 50, 52 and 54 are operated into either the conductive or vent position by the valve control signals 30, 32 and 34, respectively. Valve control signals 30, 32 and 34 are known as the up, down and ambient signals, respectively. Only one valve at a time is operated into the conductive position while the other two valves are in the vent position. Thus there is a constant flow of air from the pump 48 to each of the valves 50, 52 and 54, thereby maintaining a supply of air and its components at the valves which closely represents the air and its components at the inlet 62. The inlet 62 is located at the position or level where it is desired to collect the sample containing the component. The constant air flow eliminates the effects of inertia and back pressure which might inhibit the rapid conduction and delivery of the air sample to the canisters once the valve opens in the conductive position. The venting and use of the two-way valves also allows the airflow in each passageway and into each canister to terminate rapidly and also allows the air flow to rapidly initiate into a different passageway and canister without substantial restriction, as will occur when the vertical air velocity fluctuates rapidly in the up and down directions. Preferably, the length of the passageways 70, 72 and 74 are short to reduce the delay time between intake of air at inlet 62 and its delivery into the canisters 56, 58 and 60. In the preferred embodiment, the canisters 56, 58 and 60 are Teflon TM bags which are capable of expanding to receive the air samples delivered thereto without creating a back pressure that would restrict the flow of air samples into them. The material from which the canisters are made should also inhibit the chemical or other interaction or attraction of the component therewith, so that the quantity of the component collected in the samples can be readily determined in the laboratory. Of course, the component should be one that can be stored. Some possible alternatives to the above arrangement might use evacuated containers which would eliminate the need for a pump; use a collection medium which is not a hollow canister; use an alternative arrangement for directing the air into the canisters; or use a long inlet tube and compensate for the inherent delays associated with the transportation of the samples along the length of the tube.

Details of the operational program or the processing steps achieved by the computer processor 20 to achieve conditional sampling, and those additional steps required for the measurement of the flux of the component, some of which are not performed by the computer processor, are illustrated in FIG. 5. The first step is to start (82) the program. The vertical velocity of the air movement is next obtained (84) from the air velocity measurement subsystem as has been previously described. Each value representative of the averaged vertical velocity, represented by the symbol W, is then stored (86) for later use. Then, the magnitude (absolute value) of the averaged measured vertical velocity $|W|$ is compared (88) to a selected predetermined threshold value of vertical velocity known as $W_o$. The threshold value $W_o$ is selected both to increase the accuracy of the flux measurement as will be described below and to reduce the frequency of valve openings and closings which would occur with slight variations in the up and down movement of the air. The threshold value assures that small fluctuations of vertical velocity about the zero point do not cause the valves to switch positions on a repeated, rapid basis. If the threshold value is not exceeded, valves 50 and 52 remain in their vent positions, and valve 54 remains in the conductive position.

The predetermined threshold value $W_o$ is selected based on the anticipated ambient concentration of the component and the anticipated flux. Thus, the selection of the predetermined threshold value $W_o$ controls the sensitivity of the flux measurement. When it is desired to measure low levels of flux or when there is a low ambient concentration of a component, the threshold $W_o$ will be set to a relatively high value. The threshold may be changed or selected by use of the terminal/monitor 18 (FIG. 1), at the beginning of each sampling time period. Analysis of the component concentration collected in the ambient canister 60 (FIG. 4) from an immediately previous sampling time period or from a trial sampling time period may be useful in establishing the threshold. In most cases the threshold $W_o$ is established empirically. As will be described below in greater detail, the selection of a threshold $W_o$ determines the coefficient of proportionality.

If the threshold value $W_o$ is exceeded by the measured vertical velocity, the direction of the measured vertical velocity is tested (90). If the measured direction is up, valve 50 is operated (92) to the conductive position and valves 52 and 54 are operated (92) to the vent positions. An air sample is thereby collected in the up canister 56. If the vertical velocity is down, valve 52 is operated (94) to the conductive position and valves 50 and 54 are operated (94) to the vent positions. An air sample is thereby collected in the down canister 58.

If the threshold value $W_o$ is not exceeded by the magnitude of the measured vertical velocity as determined by the test (88), the valve 54 is operated (96) to the conductive position and the valves 50 and 54 are operated (96) to the vent positions. The air sample is directed into the canister 60 for collection. The use of the canister 60 and the collection of air samples in it is for the purpose of determining the ambient concentration of a component in the air. This information may be used to assist in setting a threshold $W_o$ in a subsequent measurement, or for other scientific and measurement purposes.

Next, the processor tests (98) if the predetermined sampling time period has expired since the start (82). If not, there is more data to be collected and the program returns (100) to start (82). A loop of steps (82) through (100) and back to (82) is performed at the sensing interval frequency. An appropriate delay (not shown) may be built into this loop of steps if the steps are executed more quickly than the sensing interval. If, however, the predetermined sampling time period has expired (98), the conditional sampling aspects of the invention are completed and the calculations resulting in the flux of the particular component are next accomplished, preferably at a later time and after the quantity of the particular component has been chemically determined from analysis.

The measurement of flux commences with the processor calculating (102) the standard deviation of each of the vertical velocities which have been previously stored (86). To calculate the standard deviation, each of the individual stored values of averaged vertical velocity W are summed together and divided by the total number of vertical velocities recorded, thus giving a value of the mean vertical velocity represented by the symbol $\overline{W}$. This mean vertical velocity $\overline{W}$ will normally be equal to zero because over a sufficiently long time period, for example, 30 minutes, the mean tends toward zero as a fact of nature. Next, each of the individual stored values of vertical velocity W is subtracted from this mean vertical velocity $\overline{W}$. Each difference is multiplied by itself, or squared, and then each of these squared products is summed together. The square root is then taken of this sum of squared products and the result is known as the standard deviation a. Calculation of the standard deviation is shown by the following equation:

$$\sigma = \sqrt{\Sigma (\overline{W} - W)^2} \qquad (A)$$

The standard deviation $\Gamma$ is a quantity which represents the average amount that each individual vertical velocity value deviated from the mean vertical velocity.

The next step (104) is performed externally to the apparatus shown in FIG. 1. The contents of the canisters 56, 58 and 60 (FIG. 3) are analyzed (104) to determine the component concentration in each.

Lastly, the flux is calculated (106). To do this, the concentration of the component in the down canister 58 is subtracted from the concentration of the component in the up canister 56. This difference is next multiplied by the standard deviation $\sigma$ of the vertical velocity. This product is next multiplied by a coefficient of proportionality, b, which has been discovered to provide accurate results at a value of approximately 0.6 under most average sampling conditions but which may vary relative to the magnitude of the ratio of the threshold value $W_o$ to the standard deviation $\sigma$. The resulting product is equal to the flux of the desired component. Calculation of the flux is represented by the following equation:

$$Flux = (b) (\sigma)(C_{up} - C_{down}) \qquad (B)$$

Step (108) represents the end of processing.

Calculation of the flux may be achieved by use of the computer processor 20 (FIG. 1), in which case data of the calculated component concentration (104) must be entered into the computer 20 at the terminal/monitor 18. If calculated external to the computer processor 20, the standard deviation values must be read from the processor at the terminal/monitor 18.

The coefficient of proportionality, b, was discovered through empirical studies. As previously mentioned, nearly instantaneous sensors of temperature and humidity exist, which makes possible the use of the instantaneous flux measurement technique. Thus, data was available for correlation of the present invention with accurate data from the instantaneous technique. The data from previous instantaneous measurements was employed in a computer simulation of the present invention. It was discovered that the results from the instantaneous measurement and the results from the conditional sampling technique were always proportional to each other for any given component and that a coefficient of proportionality, b, would scale the simulated result from the conditional sampling technique to a value equal to the result obtained by instantaneous measurement.

In most typical situations the coefficient of proportionality b will be near 0.6, but the value is not a constant, as it varies slightly as a function of the ratio of the threshold value $W_o$ to the standard deviation a as shown in FIG. 6. It can be seen that when a threshold value much smaller than the standard deviation is used, b is approximately 0.6. On the other hand, when a threshold value which more nearly approximates the standard deviation is used, by may be considerably smaller. The relationship or equation, illustrated by the graph of FIG. 6 may be programmed into the computer processor 20 (FIG. 1) so that the value of b better complies with empirical studies.

A relatively small value of b is desirable for measuring relatively low levels of flux. Examination of equation (B), for the measurement of flux, reveals that for a specific flux level under a fixed vertical air velocity condition ($\sigma$ remains the same), the value of b and the difference of ($C_{up} - C_{down}$) are inversely proportional to each other. Therefore, reduction in the value of b caused by selecting a relatively higher value of $W_o$ will cause the difference of ($C_{up} - c_{down}$) to increase. Increasing this difference is important if the difference in collected concentrations of the components is barely large enough to be resolved by the laboratory measuring. Conversely, it can be seen that if $W_o$ is selected to be too large, the vertical velocity may never exceed the threshold and no samples will be collected. For these reasons, a predetermined value of $W_o$ will be selected to match the prevailing flux and vertical air velocity conditions.

As has been described above, the conditional sampling technique for flux measurement of the present invention achieves substantial advantages and improvements. First of all, there is no need for accurate, precise movement of valves opening proportional to the vertical air velocity, as is required in the prior art eddy-accumulation technique. The problem of instantaneously measuring the components of the air is avoided. The data obtained from the conditional sampling technique of the present invention is believed to be more accurate in most circumstances than that obtained from the eddy-accumulation technique. Other advantages and improvements will be apparent after comprehension of the present invention.

A presently preferred embodiment of the present invention has been described above with a degree of specificity. The invention itself, however, is defined by the scope of the appended claims.

The invention claimed is:

1. Apparatus for determining the vertical flux of a component carried by a vertically moving gas in an ambient environment over a predetermined sampling item period, comprising:

means or measuring the magnitude and direction of the vertical velocity of said moving gas and for supplying a gas movement signal indicative of said magnitude and direction;

control means responsive to said gas movement signal for comparing the absolute value of said magnitude of said vertical gas velocity to a predetermined threshold value, and for supplying (a) an up signal upon said gas movement signal including that said measured vertical gas velocity is in an upward direction and said magnitude of the measured vertical gas velocity exceeds said predetermined threshold value, and for supplying (b) a down signal upon said gas movement signal indicating that said measured vertical gas velocity is in a downward direction and said magnitude of the measured vertical gas velocity exceeds said predetermined threshold value;

component collection means comprising:
a first and a second reservoir means for each receiving and containing samples of said gas and said component,
valve means responsive to said up and down signals for conducting samples of said gas and said component from the environment into said first or second reservoir means respectively;
said valve means open substantially fully without restriction to conduct one of said samples to said first reservoir means upon receipt of said up signal and closing to fully terminate the flow of said one sample to said first reservoir means upon termination of said up signal;
said valve means opening substantially fully without restriction to conduct one of said samples to said second reservoir means upon receipt of said down signal and closing to fully terminate the flow of said one sample to said second reservoir means upon termination of said down signal;
said control means periodically storing data indicative of said measured magnitude and direction and calculating the standard deviation of said magnitude of the vertical velocity of said gas from said stored data during said sampling time period; and
said control means further multiplying said standard deviation by a predetermined coefficient and the difference in concentrations of said component conducted into said first and second reservoir means.

2. Apparatus as defined in claim 1 wherein:
said component collection means or other comprises a third reservoir means;
said control means further supplies an ambient signal upon said gas movement signal indicating that the absolute value of said magnitude of the measured vertical gas velocity does not exceed said predetermine threshold value; and
said valve means is further responsive to said ambient signal for opening substantially fully without restriction and conducting a sample of said gas and said component from the environment into said third reservoir means, and is operative in the absence of said ambient signal or closing to fully terminate the flow of said sample to said third reservoir means.

3. Apparatus as defined in claim 1 further comprising:
pump means for supplying a flow of said gas from the environment to said valve means.

4. Apparatus as defined in claim 3 wherein the flow of said gas is continual.

5. Apparatus as defined in claim 4 wherein said valve means vents the gas flow from said pump means to the atmosphere when said valve means closes to fully terminate the flow of said sample to said first and second reservoir means.

6. Apparatus as defined in claim 1, wherein:
said control means in further operative for determining when said sampling time period has expired.

7. A method for determining the vertical flux of a component carried by a vertically moving gas in an ambient environment over a predetermined sampling time period, comprising:
measuring the magnitude and direction of the vertical velocity of said moving gas;
periodically storing stad indicative of said measured magnitude and direction of said vertical gas velocity;
calculating the standard deviation of said measured magnitude of the vertical as velocity from said stored data during said sample in time period;
establishing a predetermine threshold value which is greater than zero;
comparing the absolute value of said magnitude of said measured vertical gas velocity to said predetermined threshold value;
collecting samples of said gas and said component in a first and a second reservoir by selectively creating a flow of said gas and said component from the ambient environment to said first and second reservoir;
admitting said samples to said first reservoir without substantially restricting its flow upon the direction of said measured vertical gas velocity being in an upward vertical direction and said absolute value of said measured vertical as velocity exceeding said predetermined threshold value, and terminating the flow of said samples to said fist reservoir upon the direction of said measured vertical as velocity being not in the upward vertical direction or said absolute value of said measured vertical gas velocity not exceeding said predetermined threshold value;
admitting said samples to said second reservoir without substantially restricting its flow upon the direction of said measured vertical gas velocity being in a downward vertical direction and said absolute value of said measured vertical gas velocity exceeding said predetermined threshold value, and terminating the flow of said samples to said second reservoir upon the direction of said measured vertical gas velocity being not in the downward vertical direction or said absolute value of said measured vertical gas velocity not exceeding said predetermined threshold a value;
determining the concentration of said components each of said samples stored in said first and second reservoir;
determining the flux of said component by multiplying the difference concentration of said component contained in said first and second reservoir, by a predetermined coefficient and said standard dedication of said measured magnitudes of the vertical gas velocity and
providing a third reservoir in which to collect said samples of said gas and said component; and
admitting said samples to said third reservoir when the measured vertical gas velocity does not exceed said threshold value.

8. A method as defined in claim 7 further comprising:
subtracting the value of said determined component concentration of said samples stored in said second reservoir from the value of said determined component concentration of said samples stored in said first reservoir.

9. A method as defined in claim 8, further comprising:
multiplying the value of said calculated standard deviation by the difference in said determined component concentration between the samples in said first and second reservoir.

10. A method as defined in claim 9, further comprising:
multiplying the product of the calculated standard deviation and the determined difference in concentration by a coefficient of proportionality.

11. A method as defined in claim 10, further comprising:
varying the value of the coefficient of proportionality by the ratio of the threshold value to the standard dedication.

12. A method as defined in claim 7 further comprising:
establishing different predetermined threshold values for the predetermined upward and downward measured vertical gas velocities at which to admit said samples to said first and second reservoir, respectively.

13. A method as defined in claim 7 further comprising:
determining the concentration of said component in said samples stored in said third reservoir.

14. A method as defined in claim 13 further comprising:
establishing a predetermined value for said threshold value from said determined concentration of said components said samples stored in said third reservoir.

15. A method for determining a vertical flux of a predetermining component carried by a vertically moving gas in the ambient environment, comprising:
measuring the magnitude and direction of the vertical velocity of said moving gas;
periodically storing values indicative of said measured magnitude and direction of said vertical gas velocity;
collecting samples of said gas and said component in first and second reservoir by selectively creating a flow of samples front the ambient environment to said first and second reservoir;
admitting each sample to said first reservoir without substantially restricting its flow upon the direction of said measured vertical gas velocity being in an upward vertical direction and terminating the flow of said samples to said first reservoir upon the direction of said measured vertical gas velocity being not in the upward vertical direction;
admitting each sample to said second reservoir without substantially restricting its flow upon the direction of said measured ethical gas velocity being in a downward vertical direction and terminating he flow of said samles to said second reservoir upon the direction of said measured vertical gas velocity being not in the downward vertical direction;
determining the concentration of said component in search of said samples stored in said first and second reservoir;
calculating the standard deviation of said measured magnitudes o the vertical gas velocities from said stored values;
subtracting the value of said determined component concentration of said samples stored in said second reservoir from the value of said determined concentration of said samples stored in said first reservoir;
multiplying the value of said calculated standard deviation by the difference in said determined component concentration between the samples stored in said first and second reservoir; and
multiplying the product of said calculated standard deviation and the difference in said determined component concentration by a coefficient of proportionality.

16. A method as defined in claim 15 further comprising:
establishing a predetermined upward threshold level which the magnitude of said measured vertical gas velocity must exceed before a sample is admitted to said first reservoir and below which the flow of said sample to said first reservoir is terminated; and
establishing a predetermined downward threshold level which the magnitude of said measured vertical gas velocity must exceed before a sample is admitted to said second reservoir and below which the flow of said sample to said second reservoir is terminated.

17. A method as defined in claim 16 further comprising:
establishing the predetermined upward and downward threshold levels at the same magnitude.

18. A method as defined in claim 17, further comprising:
varying the value of the coefficient of proportionality by the ratio of the threshold level to the standard deviation.

* * * * *